US007758856B2

(12) United States Patent
Hughes et al.

(10) Patent No.: US 7,758,856 B2
(45) Date of Patent: Jul. 20, 2010

(54) BACTERIOPHAGE FOR THE TREATMENT OF BACTERIAL BIOFILMS

(75) Inventors: Gavin Hughes, Mid-Glamorgan (GB); James Taggart Walker, Salisbury (GB); Richard Sharp, Salisbury (GB); Anthony Hart, Wirral (GB)

(73) Assignee: Biocontrol Limited, Southampton (GB)

( * ) Notice: Subject to any disclaimer, the term of this patent is extended or adjusted under 35 U.S.C. 154(b) by 1058 days.

(21) Appl. No.: 10/541,716

(22) PCT Filed: Jan. 12, 2004

(86) PCT No.: PCT/GB2004/000073
§ 371 (c)(1), (2), (4) Date: Jan. 26, 2006

(87) PCT Pub. No.: WO2004/062677
PCT Pub. Date: Jul. 29, 2004

(65) Prior Publication Data
US 2006/0140911 A1    Jun. 29, 2006

(30) Foreign Application Priority Data
Jan. 10, 2003  (GB) .................................. 0300597.2

(51) Int. Cl.
*A61K 38/51* (2006.01)
*A61K 39/12* (2006.01)
(52) U.S. Cl. .................. 424/93.6; 424/94.6; 435/235.1
(58) Field of Classification Search .................. None
See application file for complete search history.

(56) References Cited

U.S. PATENT DOCUMENTS

| 4,678,750 | A | 7/1987 | Vandenbergh et al. |
| 5,242,902 | A | 9/1993 | Murphy et al. |
| 5,582,825 | A | 12/1996 | Sakaguchi et al. |
| 5,641,497 | A | 6/1997 | Bevins et al. |
| 6,121,036 | A | 9/2000 | Ghanbara et al. |
| 2002/0037260 | A1 | 3/2002 | Budny et al. |

FOREIGN PATENT DOCUMENTS

| WO | WO89/11291 | 11/1985 |
| WO | WO94/21672 | 9/1994 |
| WO | WO95/32287 | 11/1995 |
| WO | WO02/07742 | 1/2002 |

OTHER PUBLICATIONS

Lee et al. (J. Bacteriol., 92:1821-1827, 1966).*
Nairn (Chapter 86 in Remington: The science and practice of pharmacy, vol. II, 1995, pp. 1495-1523).*
Corbin, Brian D. et al., "Bacteriophage T4 multiplication in a glucose-limited *Escherichia coli* biofilm", Can. J. Microbiol., vol. 47, pp. 680-684, (2001).
Doolittle, M. M., et al., "Lytic infection of *Escherichia coli* biofilms by bacteriophage T4", Can. J. Microbiol., vol. 41, pp. 12-18, (1995).
Doolittle, M. M., et al., "Tracing the interaction of bacteriophage with bacterial biofilms using fluorescent and chromogenic probes", Journal of Industrial Microbiology, vol. 16, pp. 331-341, (1996).
Hancock, Robert E. W., et al., "Peptide antibiotics", Antimicrobial Agents and Chemotherapy, vol. 43, No. 6, pp. 1317-1323, (1999).
Hanlon, Geoffrey W., et al., "Reduction in exopolysaccharide viscosity as an aid to bacteriophage penetration through pseudomonas aeruginosa biofilms", Appl. Environ. Microbiol., vol. 67, No. 6, pp. 2746-2753, (2001).
Hatch, Richard A., et al., "Alginate lyase promotes diffusion of aminoglycosides through the extracellular polysaccharide of mucoid *pseudomonas aeruginosa*", Antimicrob. Agents Chemother., vol. 42, No. 4, pp. 974-977, (1998).
Hughes, Kevin A., et al., "Biofilms susceptibility to bacteriophage attack: the role of phage-borne polysaccharide depolymerase", Microbiology, vol. 144, pp. 3039-3047, (1998).
Hughes, G., et al., "Biofilms, bacteriophage interactions and bacteriophage therapy", Bioline, pp. 325-331, (2001).
Mah, Thien-Fah C., et al., "Mechanisms of biofilm resistance to antimicrobial agents", Trends in Microbiology, vol. 9, No. 1, pp. 34-39, (2001).
Merril, Carl., et al., "The prospect for bacteriophage therapy in Western medicine", Nature Reviews: Drug Discovery, vol. 2, pp. 489-497, (2003).
Nickel, J. C., et al., Tobramycin resistance of pseudomonas aeruginosa cells growing as a biofilm on urinary catheter material, Antimicrobial Agents and Chemotherapy, pp. 619-624, (1985).
Roy, B., et al., "Biological inactivation of adhering listeria monocytogenes by listeriaphages and a quaternary ammonium compound", Appl. Environ. Microbiol., vol. 59, No. 9, pp. 2914-2917, (1993).
Soothill, J. S., Bacteriophage prevents destruction of skin grafts by *pseudomonas aeruginosa*, Burns, vol. 20, No. 3, pp. 209-211, (1994).
Stewart, Philip S., et al., "Antibiotic resistance of bacteria in biofilms", The Lancet, vol. 358, pp. 135-138, (2001).
Sutherland, Ian W., et al., "Polysaccharides in biofilms and their interactions with phage and antimicrobials", Bioline, pp. 179-187, (1999).
Sutherland, Ian, W., "Polysaccharases for microbial exopolysaccharides", Carbohydrate Polymers, vol. 38, pp. 319-328. (1999).

(Continued)

*Primary Examiner*—Robert B Mondesi
*Assistant Examiner*—Brian J Gangle
(74) *Attorney, Agent, or Firm*—Evan Law Group LLC

(57) ABSTRACT

The present invention provides a composition for treating a bacterial biofilm, comprising a first bacteriophage that is capable of infecting a bacterium within said biofilm, and a first polysaccharide lyase enzyme that is capable of degrading a polysaccharide within said biofilm. The composition preferably further comprises a pharmaceutically-acceptable antimicrobial agent, and may also include a DNase. Also provided are modified bacteriophages, methods of creating modified bacteriophages, use of said compositions and bacteriophage for treating biofilms, and methods for treating biofilms using the bacteriophages and compositions of the invention.

40 Claims, 5 Drawing Sheets

OTHER PUBLICATIONS

Figure 1:
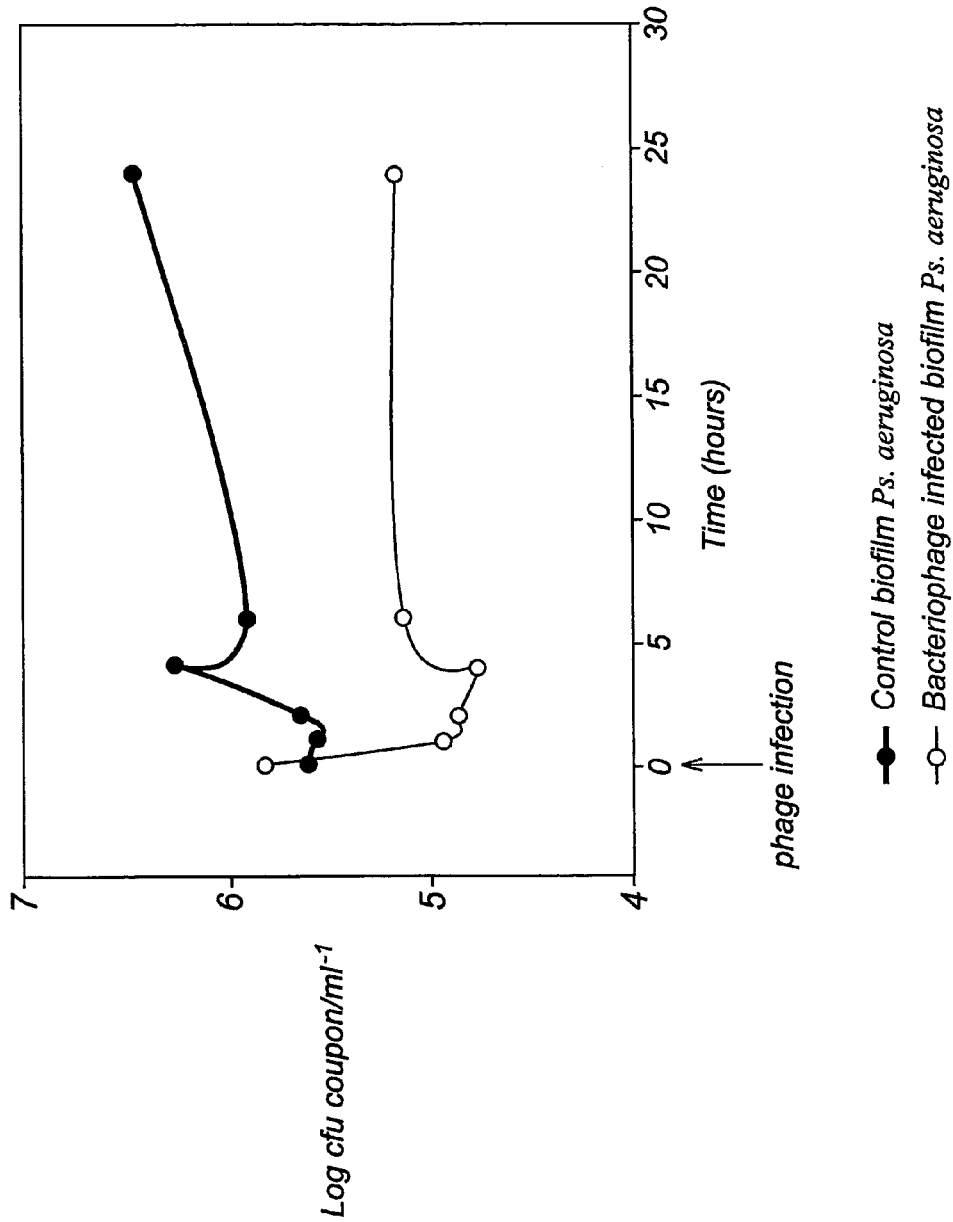

Tait. K., et al., "The efficacy of bacteriophage as a method of biofilm eradication", Biofouling, vol. 18, No. 4, pp. 305-311, (2002).

Wood, Helen I., et al., "Susceptibility of *staphylococcus epidermis* biofilm in CSF shunts to bacteriophage attack", Eur, J. Pediatr. Surg., vol. 11, Suppl. 1, S56-57, (2001).

UK Search Report for GB 0300897.2 dated Jun. 30, 2003.

Internatioanl Search Report for PCT/GB2004/000073 dated Jun. 23, 2004.

Barrow et al., "Use of lytic bacteriophage for control of experimental *Escherichia coli* septicemia and meningitis in chickens and calves," Clin Diagn Immunol, 5, pp. 294-298, 1998.

Biswas et al., "Bacteriophage Therapy rescues mice bacteremic from a clinical isolate of vancomycin-resistant *Enterococcus faecium*," Intfect. Imm., 70, pp. 204-210, 2002.

Kitamikado et al., "Method designed to detect alginate-degrading bacteria," Appl. Environ. Microbiol., 56, pp. 2939-2940, 1990.

Smith et al., "Effectiveness of phages in treating experimental *Escherichia coli* diarrhea in calves, piglets and lambs," J Gen Microbiol, 129, pp. 2659-2675, 1983.

Smith et al., "The control of experimental *Escherichia coli* diarrhea in calves by means of bacteriophages," J Gen Microbiol, 133, pp. 1111-1126, 1987.

Weiner et al., "Structure, function and immunochemistry of bacterial *exopolysaccharides*," J Ind Microbiol, 15, pp. 339-346, 1995.

\* cited by examiner

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggactgaact tcttcgcc                                                   18

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctgctgctg gatcggc                                                    17

BACTERIOPHAGE FOR THE TREATMENT OF BACTERIAL BIOFILMS

SEQUENCE LISTING

The instant application contains a Sequence Listing which has been submitted via EFS-Web and is hereby incorporated by reference in its entirety. Said ASCII copy, created on Feb. 18, 2010, is named MSQ0405.txt, and is 850 bytes in size.

The present invention concerns compositions for treating bacterial biofilms using bacteriophages, modified bacteriophages, and associated methods and uses of bacteriophages.

There is an urgent need in the near future to develop alternative anti-microbials to replace antibiotics for treating a whole spectrum of bacterial diseases. Action is needed due to an alarming increase of antibiotic resistance that poses a very real threat to modern medicine. Intermittent treatment and the re-emergence of infection tends to create selective pressure towards producing resistant microbial strains, and the nature of hospital environments and the sheer number of routine operations make the spread of infection more hazardous. Additionally, the ease and frequency of international travel assists in the spread of resistant bacteria throughout the world.

Many pathogenic microorganisms reside within biofilms, which biofilms cause additional problems when designing new anti-microbial agents. In this regard, bacteria and fungi growing as a biofilm rather than in free-floating (ie. planktonic) forms tend to be particularly resistant to anti-microbial agents and to be particularly difficult for the host immune system to render an appropriate response.

Examples of biofilm-associated microbial infections include infections of:— oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses, internal fixation devices, and percutaneous sutures; and tracheal and ventilator tubing. Both indwelling and subcutaneous biomedical implants or devices are potential sites for microbial infections and represent important targets for the control of infection, inflammation, and the immune response. Biomedical systems such as blood oxygenators, tracheal lavage, dental water units, and dialyzers are also susceptible to bacterial contamination and biofilm formation.

A biofilm is an accumulation of microorganisms embedded in a matrix of polysaccharide. Biofilms may form on solid biological or non-biological surfaces and are medically important, accounting for over 80 percent of microbial infections in the body.

Virulence and pathogenicity of microorganisms is often enhanced when growing as a biofilm, and new strategies are therefore required to control biofilm formation and development. For example, US20002/0037260 describes a system in which an anti-microbial agent (eg. an antibiotic) and a biofilm-degrading enzyme (eg. alginate lyase) are each coupled to anchoring molecules, which help localise and maintain said agent and enzyme at the site of the biofilm where they can exert their effect.

However, biofilms are difficult to treat with anti-microbials and bacterial resistance to antibiotics is enhanced up to 1000-fold over the level observed when grown under planktonic conditions. In addition, biofilms increase the opportunity for gene transfer between bacteria and may be significant for the transfer of resistance genes to associated susceptible bacteria. Gene transfer can convert a previously avirulent strain into a virulent pathogen.

New, and more virulent microbial phenotypes may be expressed when growing within a biofilm.

Bacteria embedded within biofilms are resistant to both immunological and non-specific defence mechanisms of the body. Contact with a solid surface induces the expression of a bacterial enzyme, which catalyses the formation of exopolysaccharides that promote colonisation and protection.

Immune responses are only directed towards those antigens on the outer surface of the biofilm. Antibodies and other serum or salivary proteins may fail to penetrate into the biofilm. Cells within the biofilm remain hidden from antibody and complement factor recognition, and thus from subsequent white blood cell phagocytosis. The presence of biofilms can modulate cytokine synthesis, and can interrupt production of antibodies via synthesis of superantigens. Phagocytes are unable to effectively engulf a bacterium growing within a complex polysaccharide matrix attached to a solid surface. This may result in phagocytes releasing large amounts of pro-inflammatory enzymes and cytokines, leading to inflammation and destruction of nearby tissues.

As bacterial cell density within a biofilm increases, the bacteria may communicate with each other. This can lead to the secretion of low molecular weight molecules that signal when the population has reached a critical threshold. This process, called quorum sensing, is responsible for the expression of virulence factors. For example, *Pseudomonas aeruginosa* produces destructive proteases when the number of these bacteria reaches a high enough density in the airway biofilms of cystic fibrosis (CF) patients.

Accordingly, alternative curative and prophylactic approaches for tackling microbial infections within a biofilm are required.

Bacteriophage based therapies have been considered in the past for the treatment of free-floating (ie. planktonic) microbial infections. However, following the discovery of antibiotics, phage therapy was eclipsed in the 1940s, although extensive clinical research continued in Eastern Europe. In Russia and Georgia, phage are currently produced and marketed by a number of companies for the treatment of enteric disorders, bladder infections and post-operative infections.

In Britain and the United States, there has been renewed interest in the application of phage therapy since the 1980s. For example, the successful treatment of domestic animals with *E. coli* infections has been reported by Smith and Huggins (1983; 1987), and by Barrow et al. (1998). Phage have been used in treating burns infected with *P. aeruginosa*. Soothill et al (1994) have demonstrated that skin-graft rejection could be prevented in a guinea pig model by prior treatment with *Pseudomonas* phage, and in an earlier study (Soothill et al 1992) have demonstrated phage mediated protection of mice from a systemic *Pseudomonas* infection. Biswas et al. (2002) have recently reported the successful bacteriophage mediated rescue of bacteremic mice infected with vancomycin resistant *Enterococcus faecium*. Bacteriophage have also been used in the past for treatment of plant diseases, such as fireblight as described in U.S. Pat. No. 4,678,750.

However, none of the above art addresses the treatment of biofilm infections, which account for many current clinical infections, and their associated medical conditions (see Table 1).

One of the first studies to examine the interaction of bacteriophage with biofilms was reported by Doolittle et al. (1995, 1996). Biofilms of *E. coli* strains 3000 XIII developed on the surfaces of polyvinylchloride coupons in a modified Robbins device were infected and lysed using bacteriophage T4D. Similar studies with phage E79 infecting *Pseudomonas aeruginosa* indicated phage were infecting the surface organisms but access to the cells deep in the biofilm was restricted. Temperature and nutrient concentration did not appear to affect susceptibility, but low temperature and low nutrients did prolong the time for lysis to occur and slowed the spread of infection within the biofilm. The *E. coli* biofilms were relatively thin (15-30 µm) compared to the *P. aeruginosa* biofilm (150 µm).

Sutherland et al. (1999) reported that, during the early stages of biofilm development, bacteriophage have an effect on biofilm development. Surface decontamination of stainless steel and polypropylene contaminated with *Listeria monocytogenes* was evaluated using Listeriaphage. Phage suspensions at concentrations up to $3.5 \times 10^8$ pfu per ml were found to have an effect in reducing the bacterial count, which was comparable with 20 ppm solution of an industrial sterilizing agent (QUATAL), which is a quaternary ammonium compound (Roy et al. 1993). The latter paper also describes sterilization methods employing phage suspensions in combination with QUATAL.

TABLE 1

| Infections of disease | Common biofilm bacterial species |
|---|---|
| Nosocomial infections: | |
| ICU pneumonia | Gram-negative rods |
| Sutures | *Staphylococcus epidermidis* and |
| Exit sites | *Staphylococcus aureus* |
| Arteriovenous shunts | *S. epidermidis* and *S. aureus* |
| Schleral buckles | *S. epidermidis* and *S. aureus* |
| Contact lens | Gram-positive cocci |
| Urinary catheter-cystitis | *Pseudomonas aeruginosa* and Gram-positive cocci |
| Peritoneal dialysis (CAPD) peritonitis | *Escherichia coli* and other Gram-negative rods |
| IUDs | A variety of bacteria and fungi |
| Endotracheal tubes | *Actinomyces israelii* and many others |
| Hickman catheters | A variety of bacteria and fungi |
| Central venous catheters | *S. epidermidis* and *Candida albicans* |
| Mechanical heart valves | *S. epidermidis* and others |
| Vascular grafts | *S. aureus* and *S. epidermidis* |
| Biliary stent blockage | Gram-positive cocci |
| Orthopedic devices | A variety of enteric bacteria and fungi |
| Penile prostheses | *S. aureus* and *S. epidermidis* |
| Dental caries | *S. aureus* and *S. epidermidis* |
| Periodontitis | Acidogenic Gram-positive cocci (eg. *Streptococcus*) |
| Otitis media | Gram-negative anaerobic oral bacteria |
| Musculoskeletal infections | Non-typable strains of *Haemophilus influenzae* |
| Necrotizing fasciitis | Gram-positive cocci (eg. *staphylococci*) |
| Biliary tract infection | Group A *streptococci* |
| Osteomyelitis | Enteric bacteria (eg. *E. coli*) |
| Bacterial prostatitis | Various bacterial and fungal species - often mixed |
| Native valve endocarditis | *E. coli* and other Gram-negative bacteria |
| Cystic fibrosis pneumonia | Viridans group *streptococci* *P. aeruginosa* and *Burkholderia cepacia* |

* Abbreviations:
CAPD, continuous ambulatory peritoneal dialysis;
ICU, intensive care unit;
IUD, intrauterine device.

Tait et al (2002) describes another phage-based method for sterilizing work surfaces contaminated by a biofilm. In more detail, the authors describe the use of compositions containing an *Enterobacter* strain-specific bacteriophage, and compositions containing a polysaccharide deploymerase in combination with a disinfectant for sterilizing work surfaces in an industrial environment.

Bacteriophage SF153b, isolated from sewage and able to infect the biofilm-forming bacterium *Enterobacter agglomerans* 53b, was shown to possess a depolymerase specific for the exopolysaccharide of strain 53b (Hughes et al., 1998). Using a Robbins device, the phage was shown to disrupt the exopolysaccharide (EPS) of a mono-species biofilm and to infect the cells.

Hanlon et al. (2001) have recently demonstrated the ability of *P. aeruginosa* phage to diffuse through alginate gels at alginate concentrations up to 8% (wt/vol), and to bring about a 2-log reduction in the cell numbers in 20-day-old biofilms of *P. aeruginosa*. Samples of commercial alginate and purified cystic fibrosis (CF) alginate were incubated with $2 \times 10^8$ purified phage per ml for 24 h at 37° C., and the viscosity of phage-treated samples were reduced by up to 40% compared to those of controls incubated in the absence of phage. The alginate treated with phage had a lower molecular weight than untreated alginate, and the evidence suggested that the reduction in alginate viscosity was brought about by enzymic degradation derived from the bacterial host itself (ie. endogenous to the bacterial host cell).

Of the infections listed in Table 1, one of the most problematic infections to treat is that of cystic fibrosis pneumonia.

Most cystic fibrosis (CF) patients suffer from recurrent and chronic end-bronchial *Pseudomonas aeruginosa* infections. Intervention strategies include eliminating cross infection, and early aggressive antibiotic treatment. An inflammatory response occurs resulting in a shift of the organism's phenotype from non-mucoid to a mucoid phenotype. This alginate-producing phenotype then grows as an endo-bronchial biofilm, which is impossible to eradicate through antibiotic therapy.

There is therefore a need for alternative approaches for the treatment of infectious biofilms, preferably those associated with cystic fibrosis.

According to a first aspect, the present invention provides a composition for treating a bacterial biofilm, comprising a bacteriophage, and a first polysaccharide lyase enzyme (eg. an alginate lyase). The first polysaccharide lyase may be absorbed onto the surface of said bacteriophage. The composition may further comprise one or more pharmaceutically-acceptable antimicrobial agents (eg. antibiotics, and/or defensins), a second or more polysaccharide lyases (preferably different from the first), optionally adsorbed onto the surface of the bacteriophage, and/or a DNase. The bacteriophage may encode said first, second or more polysaccharide lyase, said DNase, and/or said pharmaceutically-acceptable antimicrobial agent.

The bacteriophage can penetrate biofilms and infect biofilm-associated bacteria to cause a reduction (eg. by lysis) in bacterial numbers, preferably a reduction of between about 1 and 3 logs of bacterial viable counts. Also provided are modified bacteriophages, methods of creating modified bacteriophages, compositions for treating biofilms comprising bacteriophages, and methods for treating biofilms using the bacteriophages and compositions of the invention.

In the context of the present invention, the term "first polysaccharide lyase" may embrace related enzymes known as polysaccharide depolymerases. Moreover, the "first polysaccharide lyase" of the invention is exogenous with respect to a target bacterium in the targeted biofilm. For example, the "first polysaccharide lyase" is preferably phage-encoded, phage-associated, or present as a discrete component of the composition.

The following advantages are provided by the present invention, which employs the use of a bacteriophage to target and destroy (or protect against the formation of) infectious biofilms.

Phage are self-replicating and self-limiting and may be delivered by aerosol to the lungs. The self-replicating property is an advantage when patient compliance towards regular drug therapy is poor.

Phage may be highly specific in the destruction of their targets and, unlike antibiotics, do not interfere with natural flora. Combinations of different phage may be employed in the present invention. For example, phage cocktails may be tailored to target particular bacterial types present in a targeted biofilm. In this regard, different phage may be selected to target different (or the same) bacterial strains, species or genera present in a targeted biofilm.

Phage are easy to produce and are a cost-effective form of therapy.

Phage may be formulated in combination with one or more pharmaceutically-acceptable anti-microbial agents. In this regard, combinations of different antimicrobial agents may be tailored to target different (or the same) microorganisms, which contribute towards morbidity and mortality. The pharmaceutically-acceptable anti-microbial agents of the present invention are suitable for internal administration to an animal (preferably human), and therefore exclude industrial sterilizing chemicals such as detergents, disinfectants, and ammonium-based chemicals (eg. quaternary ammonium compounds such as QUATAL). Such sterilizing chemicals are typically used in the art for sterilizing industrial work surfaces (eg. in food processing, or hospital environments), and are not suitable for administration to an animal.

Phage may be used to treat immuno-compromised individuals or patients that have an allergy to antibiotics.

Phage can be stored for very long periods with no obvious loss of activity.

Phage resistant host strains of Ps. aeruginosa can be identified quickly and new varieties of phage can be readily generated to overcome resistance.

The therapeutic use of phage has been widely used in Eastern Europe for over 60 years with no reported significant adverse effects.

The bacteriophage preferably targets one or more of the bacteria listed in Table 1.

The bacteriophage preferably targets one or more of the bacteria listed in Table 1. Particularly preferred bacterial targets include one or more of:— Staphylococcus aureus; Haemophilis influenzae; Pseudomonas aeruginosa; Burkholderia cepacia; Streptococcus pneumoniae; Stenotrophomonas maltophilia; Alcaligenes xylosoxidans; non-tuberculous mycobacteria; Mycobacterium bovis; Mycobacterium smegmatis; Mycobacterium tuberculosis; Burkholderia multivorans; Burkholderia stables; and Burkholderia vietnamesis. In terms of simple nomenclature, the bacteriophages are usually identified by reference to the bacteria that they infect. Thus, a bacteriophage that infects a mycobacterium may be referred to as a mycobacteriophage.

The present invention is preferably concerned with the treatment of biofilm-associated opportunistic infections, and particularly with the treatment of such infections in lung biofilms (eg. those associated with CF patients). Thus, the highly preferred bacterial targets of the present invention are Pseudomonas sp. and/or Burkholderia sp., especially Ps. aeruginosa and/or B. cepacia.

Preferred bacteriophage for use against the above bacterial targets have a high affinity for the bacterial target strain, and a high burst size. Said phage preferable encode a polysaccharide lyase (eg. an alginate lyase). Where the bacterial target is Ps. aeruginosa, preferred bacteriophage include φGH4, φGH6, φGH13 and φGH14.

A biofilm matrix typically comprises a high proportion of water (see Table 2), although this would depend on the specific biofilm system examined. Apart from water and microbial cells, the biofilm matrix is a complex of absorbed nutrients and metabolites, products from cell lysis, particulate material from the immediately surrounding area and secreted polymers. All major classes of macromolecules, protein, polysaccharides, DNA and RNA can be present in addition to peptidoglycan, lipids and other cell components.

Table 2—Typical Range of Biofilm Matrix Composition

| Component | % of matrix |
|---|---|
| Water | up to 97% |
| Microbial cells | 2-5% |
| Polysaccharides | 1-2% |
| Proteins | <1-2% |
| DMA and RNA | <1-2% |
| Ions (bound and free) | 1% |

The production of exopolysaccharides (EPS) is essential to the development of the architecture of the biofilm. It provides a framework into which microbial cells are inserted, and may also serve as a nutrient source for sessile cells.

In use of the present invention, a polysaccharide lyase enzyme is preferably selected such that it is capable of breaking down a component of the biofilm of interest. It is particularly preferred that the enzyme is capable of breaking down a component of the biofilm that is produced by a bacterium associated with (eg. residing within) the biofilm.

Alginate is the major extracellular product of biofilm-forming bacteria such as mucoid strains of Ps. aeruginosa. The latter chronically colonise the cystic fibrosis (CF) pulmonary cavity, and the resulting alginate glycocalyx acts as a barrier for Ps. aeruginosa sessile cells to antimicrobial agents and host defences. Thus, the mucoid form of Ps. aeruginosa is much more difficult to treat and is invariably associated with a poor prognosis for CF patients. Novel methods of eradicating this mucoid form of the organism are therefore essential for successful treatment of these chronic infections.

Alginate is a linear polysaccharide comprised of 1-4 linked β-O-mannuronic acid (M) (O-acetyl substitution on 2 and/or 3 position) and α-L-guluronic acid (G) monomers, which can either be arranged in homopolymeric (poly-guluronate GGGG, poly-mannuronate MMMM) or heteropolymeric (random sequences MGMG) regions.

structures) may be present within a single alginate molecule. Thus, the preferred "first polysaccharide lyase" of the present invention is an alginate lyase and has a high affinity for at least one of (preferably both) M and G rich regions. The lyase may be encoded by the phage of the present invention, or may be exogenous with respect to the phage. It is also beneficial for the lyase to exhibit endo-cleaving activity (i.e. it can break up long linear alginate chains within their complex blocks of monomeric units, as opposed to exolytic activity in which monomers are removed from the ends of the polymer), thus breaking down the viscous long chained polymer into more aqueous oligosaccharide shorter chain products.

The presence of a DNase may help to break down DNA from dead patient host cells (eg. lung epithelial cells) within a biofilm, and may help to dissolve mucus components associated with a biofilm.

Defensins are a group of gene-encoded antimicrobial peptides that have been identified from a diverse range of organisms, such as vertebrates, invertebrates, plants and bacteria. In mammals, defensins are part of the innate host defence mechanism and are present in phagocytic cells and epithelial cells. They show a potent activity towards microorganisms, and are particularly useful for targeting antibiotic resistant bacteria [see Hancock, R. E. and Chapple, D. S. (1999) Antimicrobial Agents and Chemotherapy, vol. 43, No. 6, pp. 1317-1323].

By way of example, the following defensins are suitable for use in the present invention:— gramicidin S; bacitracin; polymyxin B; α-defensin (eg. rabbit source); β-defensin (eg. human source); tachyplesin (eg. crab source); bactenecin (eg. cattle source); cecropin A (eg. silk moth source); indolicidin (eg. cattle source); and nisin (eg. bacterial source). The term "defensin" embraces synthetic peptides having antimicrobial activity, which may be employed in the present invention. Examples of such synthetic peptides are provided in the above mentioned review by Hancock (1999). Of particular mention is the polymyxin family of antimicrobial polypeptides, especially polymyxin E (ie. Colistin) and polymyxin B.

Defensins (eg. polymyxins) are bactericidal in preferred concentrations of up to 8 μg ml$^{-1}$, more preferably 1-5 μg ml$^{-1}$.

Preferred defensins are those that attach to bacterial cell membranes (especially those rich in phosphatidylethanolamine), and disrupt the osmotic properties and transport mechanisms of the membrane.

Further examples of defensins, which are suitable for use in the present invention, are provided by U.S. Pat. No. 5,242,902, U.S. Pat. No. 5,641,497, WO89/11291, WO94/21672, U"2002/0037260, and WO95/32287.

Antibiotics are well known in the art, and may be employed in the present invention. Of particular mention is the aminoglycoside family of antibiotics, which were originally obtained from *Streptomyces* species, and in particular tobramycin. Antibiotics (eg. tobramycin) are bactericidal in preferred concentrations of up to 8 μg ml$^{-1}$, more preferably 1-5 μg ml$^{-1}$. A typical antibiotic dosage regime according to the present invention for treating CF patients is the administration of 80 mg of antibiotic, preferably tobramycin, by nebulisation twice a day. As there is little adsorption from the mucosa, serum levels of tobramycin are unmeasurable. Further examples of antibiotics, which are suitable for use in the present invention, are provided by US2002/0037260.

According to one embodiment of the invention, the antibiotic acts by inhibition of ribosomal protein synthesis. Preferred antibiotics according to this embodiment are members of the aminoglycoside family. A particularly preferred antibiotic according to this embodiment is tobramycin.

Another preferred class of antibiotics is the Polymxin family, particularly Polymyxins E (Colistin) and B. Colistin is bactericidal for Gram-negative bacilli including *Pseudomonas* spp. in preferred concentrations of up to 8 μg ml$^{-1}$, more preferably 1-5 μg ml$^{-1}$. Polymyxins, such as Colistin, are preferably used as topical agents due to poor absorption of these antibiotics from the gut. It is preferred that Colistin is administered as of Colistin sulphate, which is the stable water-soluble form. A typical dosage regime for CF patients is the administration of 2 mega units of Colistin by nebulisation twice a day. As there is little adsorption from the mucosa, serum levels of Colistin are unmeasurable.

According to one embodiment of the invention, the preferred antibiotic acts by attachment to bacterial cell membranes rich in phosphatidylethanolamine and disruption of the osmotic properties and transport mechanisms of the membrane. Preferred antibiotics according to this embodiment are members of the Polymyxin family, particularly Colistin.

Further antibiotics of particular mention are ciprofloxacin (preferably administered orally) and ceftazidime (preferably administered intravenously).

The bacteriophage may be a wide spectrum phage. For example, it may target several different species within a given genus, or may even target bacteria within different genera. Alternatively, the bacteriophage may be a narrow spectrum phage. For example, it may be specific to a given bacterial genus, species, or strain. The bacteriophage is capable of infecting a bacterium present in the biofilm of interest.

In a most preferred embodiment the invention provides a composition for treating a lung biofilm in a CF patient, preferably a biofilm comprising *Pseudomonas aeruginosa* and/or *Burkholderia cepacia*. The composition according to this embodiment preferably comprises a bacteriophage that encodes a polysaccharide lyase, preferably an alginate lyase enzyme. Alternatively, the enzyme may be provided exogenously.

A preferred bacteriophage according to the present invention is a bacteriophage selected from the GH group of phage such as GH4, GH6, GH13, GH14 (ECACC accession numbers 02121203, 02121202, 02121201, and 02121204 respectively, deposited by the applicant in ECACC on 12 Dec. 2002). A particularly preferred phage is bacteriophage φGH4.

Also provided is use of the composition in manufacture of a medicament for treatment of a bacterial biofilm. A preferred target is a lung biofilm in a CF patient.

Preferably the medicament is administered in more than one dose, more preferably in at least 3 separate doses (eg. per day). It is also preferred that administration of the medicament results in a reduction in the bacterial cell count of the biofilm of at least one log, preferably at least three logs.

According to a second aspect, the invention provides a bacteriophage comprising a heterologous gene encoding a polysaccharide lyase enzyme (eg. an alginate lyase). Preferably, the bacteriophage specifically infects a bacterial species or strain present in the biofilm. The polysaccharide lyase encoded by the modified bacteriophage should preferably degrade a specific polysaccharide produced by a bacterial species or strain present in the biofilm. In a particularly preferred embodiment, the biofilm comprises *Ps. aeruginosa* and/or *B. cepia*.

The bacteriophage may optionally comprise more than one heterologous gene encoding more than one polysaccharide lyase (eg. an alginate lyase). Said enzymes are preferably different, and therefore degrade different exopolysaccharide (EPS) components of a biofilm. The terms EPS and polysaccharide are used interchangeably in the biofilm context of the present invention. The bacteriophage may also encode a DNase, and/or a pharmaceutically-acceptable antimicrobial agent (eg. an antibiotic, and/or defensin).

The modified/recombinant bacteriophage, like the "composition" first aspect of the present invention, may be used to treat biofilms such as those resulting from opportunistic bacterial infections. For example, chronic lung infections in CF patients may be treated. In particular, the modified/recombinant bacteriophage may be used as part of the "composition" aspect, and thus may be employed with one or more pharmaceutically-acceptable antimicrobial agents, a second or further (preferably different) polysaccharide lyase enzyme (eg. an alginate lyase), and/or a DNase.

In another embodiment, the "composition" aspect may include two or more modified/recombinant bacteriophage. For example, the composition may include a first and second bacteriophage, wherein the first bacteriophage comprises a gene encoding a first polysaccharide lyase enzyme, and the second bacteriophage comprises a gene encoding a second polysaccharide lyase enzyme, and wherein the first and second polysaccharide lyase enzymes are not the same. The first and second bacteriophage may be the same or different.

In a related "composition" embodiment, a cocktail of naturally-occurring and modified/recombinant bacteriophages may be employed in combination. The first polysaccharide lyase may be provided exogenously or may be encoded by one or more of the bacteriophage, and additional (preferably different) lyases may be included. Not all bacteriophage employed in a composition of the present invention need encode a polysaccharide lyase. Such bacteriophage may possess, for example, enhanced bacteriolytic activity vis-a-vis other bacteriophage with respect to biofilm-associated bacteria.

Other bacteriophage suitable for use in the present invention are publicly available from the American Type Culture Collection and have the following accession numbers ATCC 12055-B1, ATCC 12055-B2, ATCC 12055-B3, ATCC 14205-B1, ATCC 14206-B1, ATCC 14207-B1, ATCC 14209-B1, ATCC 14210-B1, ATCC 14211-B1, ATCC 14212-B1, ATCC 14213-B1, ATCC 14214-B1, ATCC 15692-B2, ATCC 15692-B3, ATCC 25102-B1, ATCC BAA-26-B1, ATCC BAA-27-B1, ATCC BAA-28-B1, ATCC BAA-28-B2, ATCC BAA-29-B1, ATCC BAA-30-B1, ATCC BAA-31-B1, ATCC BAA-47-B1, ATCC BAA-79-B1, ATCC BAA-81-B1, and ATCC BAA-81-B2.

These bacteriophages were deposited with American Type Culture Collection (ATCC, 10801 University Blvd., Manassas, Va. 20110-2209, USA), under the terms of the Budapest Treaty.

The invention also provides a method of making a modified/recombinant bacteriophage capable of degrading a biofilm comprising:—
a) selecting at least one gene encoding a polysaccharide lyase enzyme that degrades a polysaccharide within said biofilm;
b) selecting a bacteriophage that is capable of infecting a bacterial species or strain residing within the biofilm; and
c) introducing at least one of the genes selected in step a) into the bacteriophage nucleic acid (eg. DNA).

In one embodiment, the bacteriophage is selected from the group consisting of GH4, GH6, GH13, GH14 (ECACC accession numbers 02121203, 02121202, 02121201, and 02121204), or bacteriophage having accession numbers ATCC 12055-B1, ATCC 12055-B2, ATCC 12055-B3, ATCC 14205-B1, ATCC 14206-B1, ATCC 14207-B1, ATCC 14209-B1, ATCC 14210-B1, ATCC 14211-B1, ATCC 14212-B1, ATCC 14213-B1, ATCC 14214-B1, ATCC 15692-B2, ATCC 15692-B3, ATCC 25102-B1, ATCC BAA-26-B1, ATCC BAA-27-B1, ATCC BAA-28-B1, ATCC BAA-28-B2, ATCC BAA-29-B1, ATCC BAA-30-B1, ATCC BAA-31-B1, ATCC BAA-47-B1, ATCC BAA-79-B1, ATCC BAA-81-B1, and ATCC BAA-81-B2.

These bacteriophages were deposited with American Type Culture Collection (ATCC, 10801 University Blvd., Manassas, Va. 20110-2209, USA), under the terms of the Budapest Treaty.

In a preferred embodiment, the polysaccharide lyase enzyme is an alginate lyase. The modified phage is preferably capable of infecting (eg. lysing) a bacterium selected from *Ps. aeruginosa* and/or *Burkholderia cepacia*.

The method may include analysis of the biofilm to identify a bacterial species or strain within the biofilm. The biofilm is preferably a clinical sample, such as a sample taken from an infected patient (eg. a lung sample taken from a CF patient).

In a preferred embodiment the bacteriophage is specific for a bacterial species or strain present in the biofilm.

In one embodiment the polysaccharide lyase enzyme recited in step a) may be selected by use of a bank of specific enzymes, which may be tested individually on the biofilm for degradative activity. Thereafter, biofilm degradation may be confirmed by turbimetric analysis, viscometry, or chromatographic analysis.

In a further (or simultaneous) method step, one or more genes encoding a second polysaccharide lyase, and/or a pharmaceutically-acceptable antimicrobial agent, and/or a DNase may be introduced into the bacteriophage nucleic acid.

It is preferred that the efficacy of the modified bacteriophage be tested in vitro prior to use against infections in a clinical context.

A bacteriophage prepared as above may be employed in the treatment of a biofilm-associated microbial infection as described in the preceding aspects of the present invention.

According to further aspect the invention provides a method of identifying a bacteriophage for use in treatment of a biofilm-associated microbial infection, which method comprises:—
a) identifying a bacteriophage that is capable of infecting a bacterial species or strain with said biofilm; and
b) confirming that said bacteriophage encodes a polysaccharide lyase that degrades a polysaccharide within the biofilm.

In a preferred embodiment, the polysaccharide lyase enzyme is an alginate lyase. The phage is preferably capable of infecting (eg. lysing) a bacterium selected from *Ps. aeruginosa* and/or *Burkholderia cepacia*.

The method may include analysis of the biofilm to identify a bacterial species or strain within the biofilm, and/or a polysaccharide component within the biofilm or a polysaccharide produced by the microorganisms of the biofilm.

The presence of polysaccharide lyase enzyme activity may be confirmed by monitoring biofilm degradation (eg. by turbimetric analysis, viscometry, or chromatographic analysis).

The biofilm is preferably a clinical sample, such as a sample taken from an infected patient (eg. a lung sample taken from a CF patient).

In a preferred embodiment the bacteriophage is specific for a bacterial species or strain present in the biofilm.

The identified bacteriophage may be modified according to the second aspect of the invention so that it encodes a further polysaccharide lyase, an antibiotic, a DNase, and/or a defensin.

The method may include a further step of testing the efficacy of the selected bacteriophage against a sample of the biofilm in vitro.

Said bacteriophage may be employed in the treatment of a biofilm-associated microbial infection as described in the preceding aspects of the present invention.

According to another aspect of the present invention there is provided a method of treating biofilm-associated infections.

In operation, the method involves administration of at least one dose, preferably at least three doses, of bacteriophage plus first polysaccharide lyase to the site of infection. Administration is preferably via aerosol delivery. The phage and first polysaccharide may be administered at the same time, prior to, or subsequently to one another.

According to a preferred aerosol delivery embodiment, the particle size in the aerosol is between 100 µm and 1 µm. In more detail, a particle size of approximately 60 µm targets biofilms in the upper respiratory tract, whereas a particle size of 2-4 µm targets biofilms at or near the alveoli. Thus, the aerosol may have a broad delivery range (ie. contain particles of 1-100 µm), or may have a narrow delivery range (eg. 2-20 µm for targeting the lower airways, or 40-100 µm for targeting the upper airways).

antibiotic, a DNase and/or a defensin, either at the same time, prior to, or subsequently to administration of the bacteriophage.

In one embodiment, the repeated use of phage and polysaccharide lyase, optionally plus a pharmaceutically-acceptable antimicrobial agent (eg. an antibiotic, and/or defensin), is employed.

The medical treatment aspect of the present invention has particular benefits in treating CF patients and helps to prevent the re-colonisation of parts of the lung by cells that have been released from the biofilm.

The above prophylactic or curative method is particularly suitable for treatment of biofilm infections of the lung and gastrointestinal tract, and biofilms present on medical devices such as catheters, intra-vascular devices, prosthetic devices and dental implants. In particular, biofilm disruption according to the present invention enables access of antimicrobial agents (eg. antibiotics, and/or defensins) and other phage to microorganisms residing deep within said biofilm. Such access is not otherwise possible with the isolated use of an antimicrobial agent.

Figure 2:
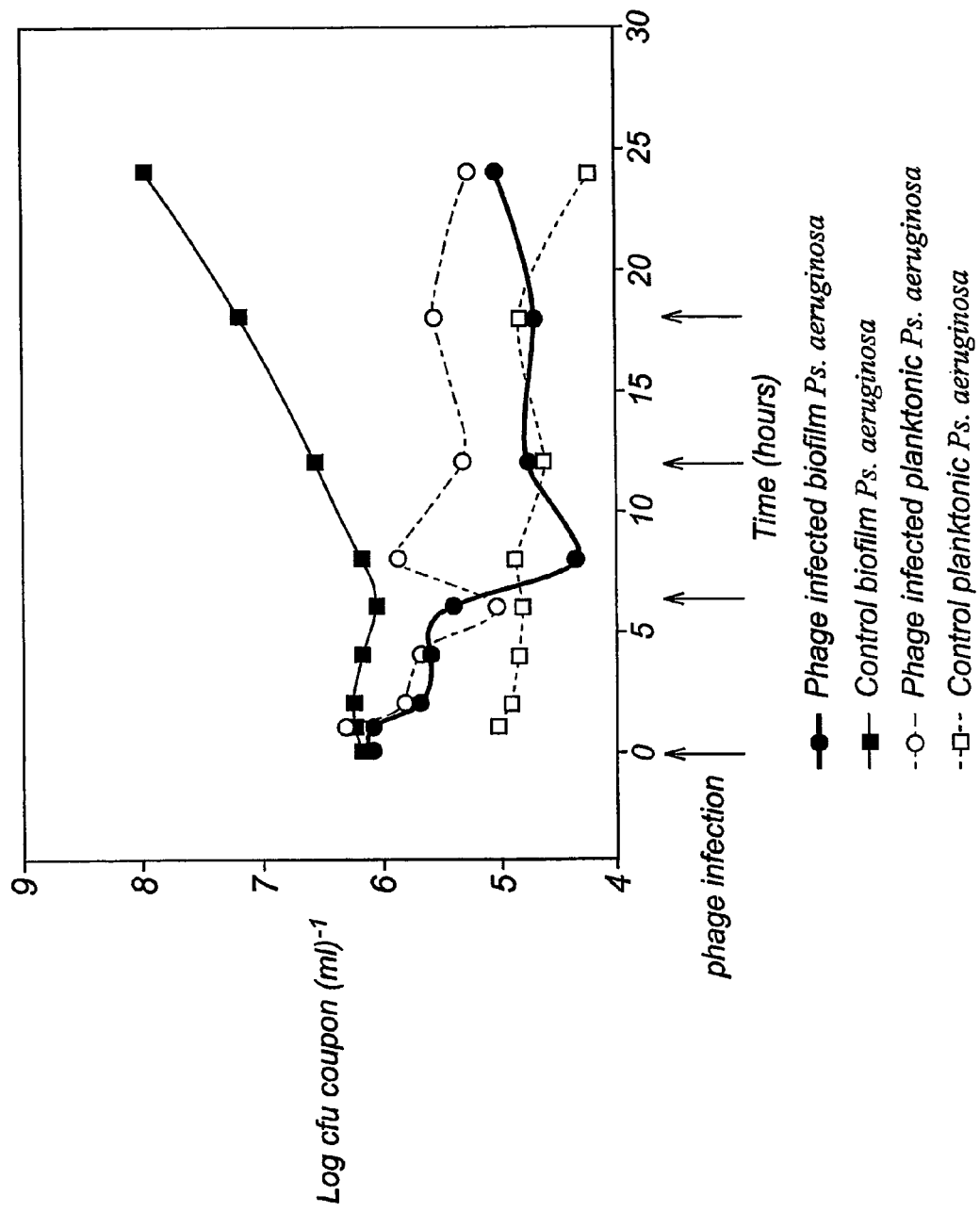
Figure 3:
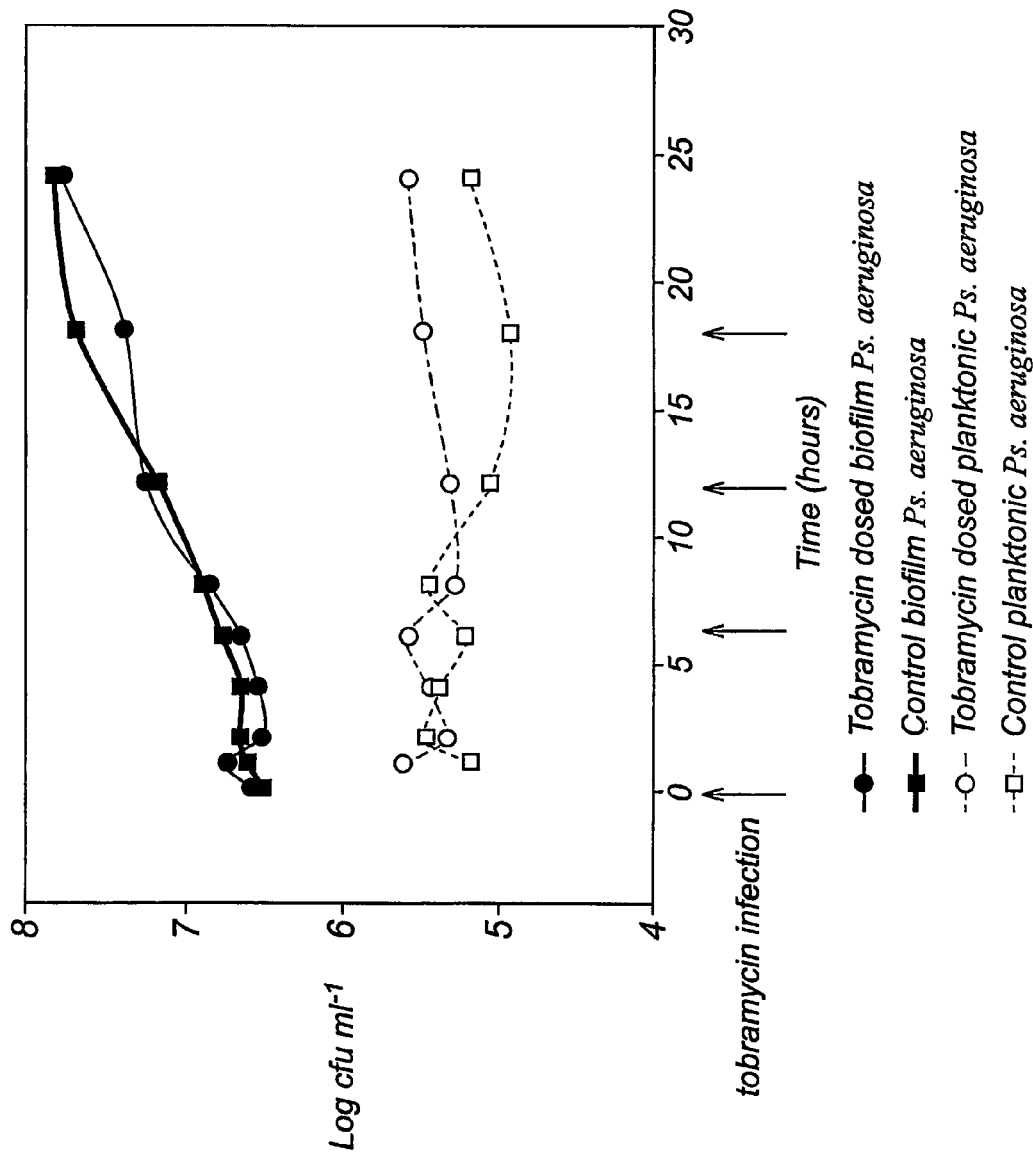
Figure 4:
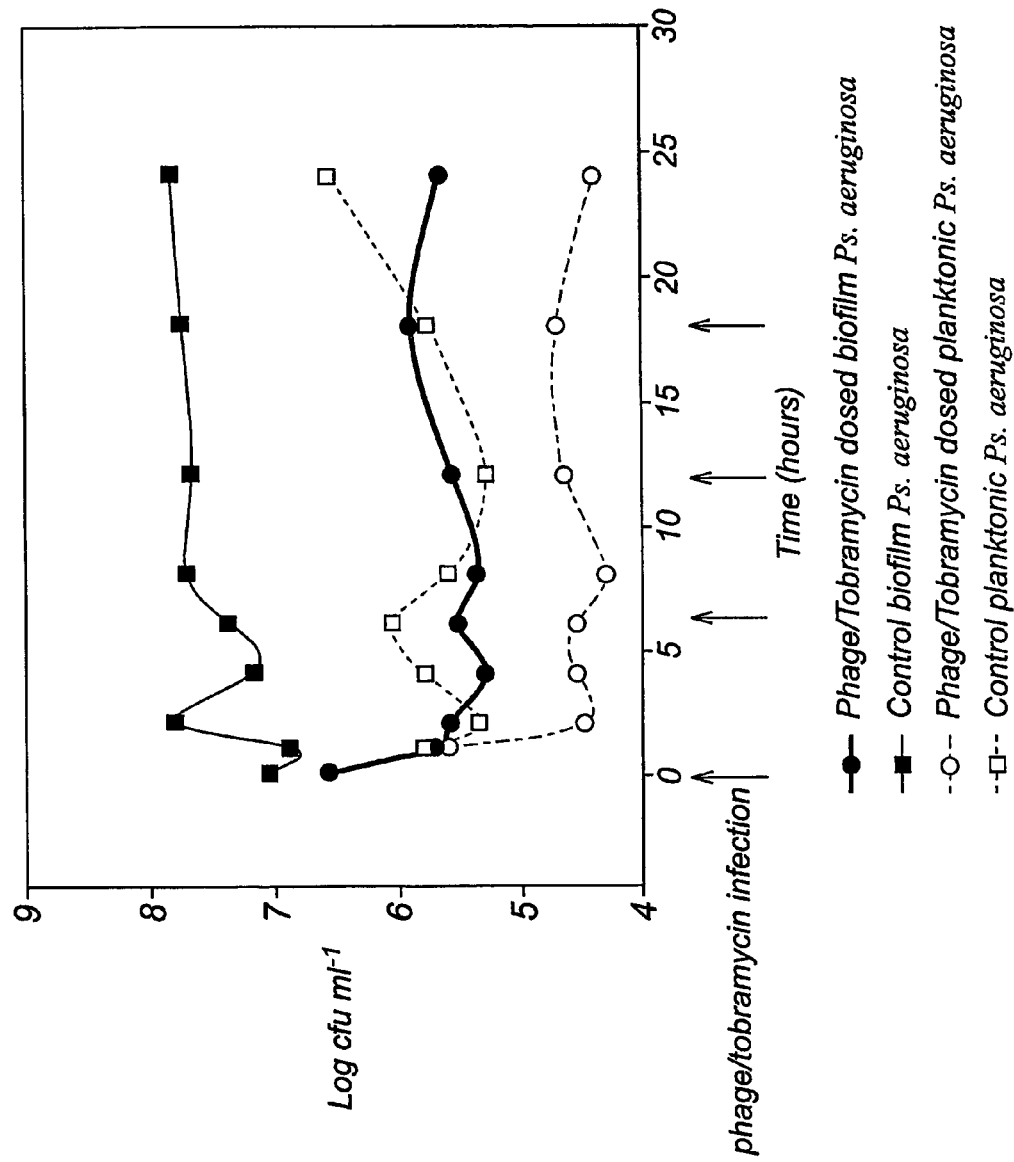

The invention is illustrated by the following drawings, in which:

FIG. 1: shows growth dynamics of control and bacteriophage infected *Ps. aeruginosa* biofilm cells in which the biofilm was infected with 1 dose of bacteriophage (10 ml of $10^9$ plaque forming units per ml {pfu ml$^{-1}$});

FIG. 2: shows growth dynamics of control and bacteriophage infected *Ps. aeruginosa* biofilm and planktonic cells in which the biofilm was infected with 4 doses of bacteriophage (10 ml of $10^9$ pfu ml$^{-1}$ every six hours for the first 18 h of experiment);

FIG. 3: shows growth dynamics of control and tobramycin dosed *Ps. aeruginosa* biofilm and planktonic cells in which the biofilm was infected with 4 doses of tobramycin at the minimal inhibition concentration (4 mg L$^{-1}$); and FIG. 4: shows growth dynamics of control and bacteriophage/tobramycin dosed *Ps. aeruginosa* biofilm and planktonic cells in which the biofilm was infected with 4 doses of bacteriophage ($10^{10}$) suspended in 10 ml of tobramycin at the minimal inhibition concentration (4 mg L$^{-1}$).

Figure 5:
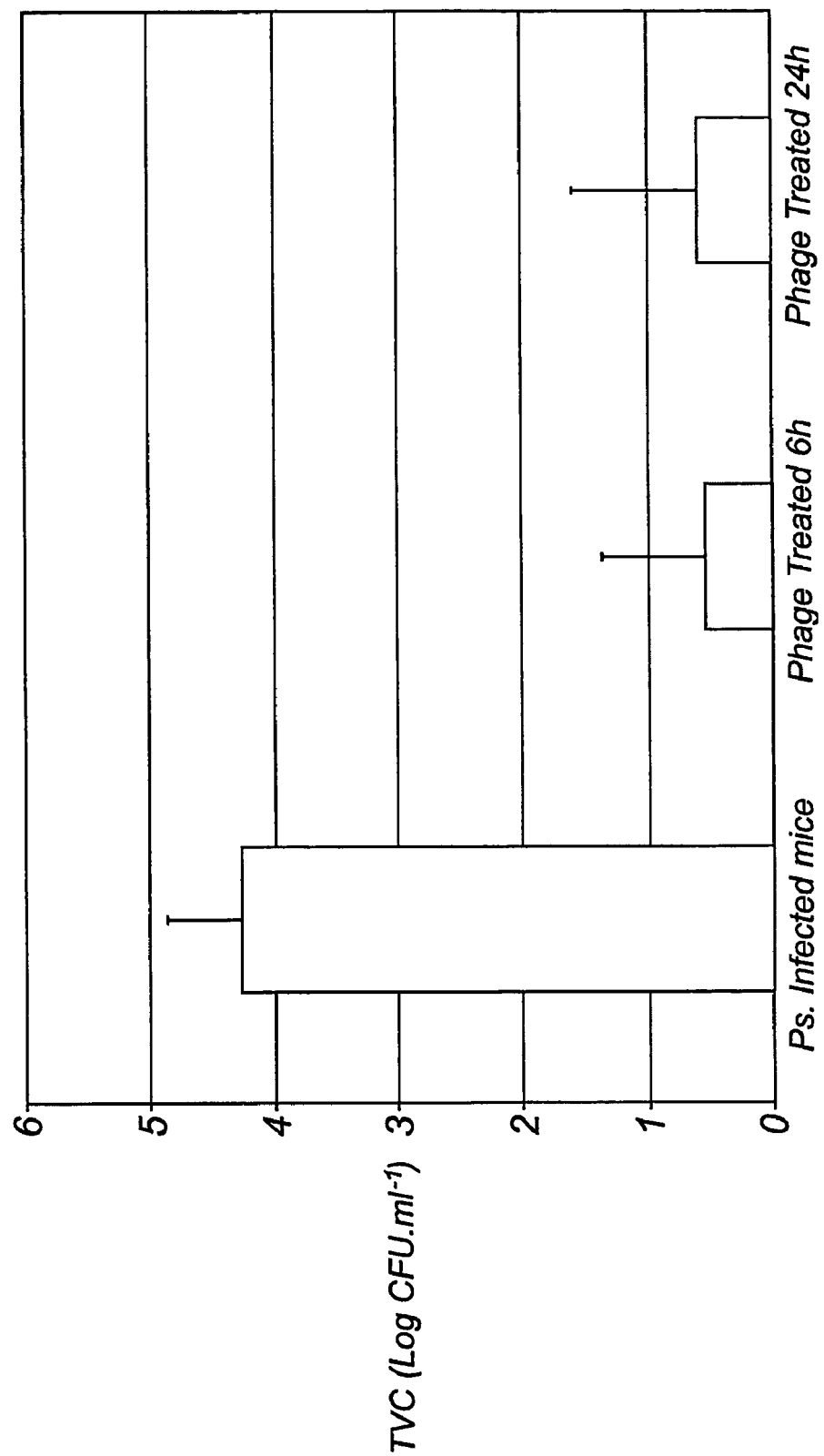

FIG. 5: shows in vivo control of a *Ps. aeruginosa* biofilm infection in mice. The mice were infected with *Ps. aeruginosa* and the infection allowed to become established. On day 10 post-infection, the mice were treated with aerosolised phage, and the number of infecting *Ps. aeruginosa* then monitored at 6 and 24 hours post-aerosol challenge. The results show a 3.75 Log CFU.ml$^{-1}$ decrease in *Ps. aeruginosa* numbers after challenge with bacteriophage.

EXAMPLE 1

Operation of a Chemostat and Robbins Device for Continuous Culture of *Pseudomonas aeruginosa* for Biofilm Investigation The present invention allows the isolation and characterisation of bacteriophage that are able to lyse clinical *Ps. aeruginosa* isolates. Bacteriophage are characterised with regard to their potential virulence based on assessment of host range, burst size and efficiency of lysis. The ability of selected phage to lyse sensitive host strains in sputum samples is evaluated and these phage evaluated further in an in vitro biofilm model simulating infection with mucoid and non-mucoid strains.

The present invention preferably relates to specific bacteriophage, which offer the potential to control *Ps. aeruginosa* induced biofilm formation and, in particular, biofilms involving the more aggressive drug resistant bacterial species that contribute significantly to morbidity and mortality in CF patients.

Background

A chemostat system has been developed to generate continuous *Pseudomonas aeruginosa* culture. The culture provide inocula for biofilm studies using a Robbins device.

The chemostat vessel consists of a 2-litre glass vessel with titanium top plates. The plate is fitted with various probes (pH, temperature and Redox) which allow the physical parameters within the vessel to be monitored and maintained under defined controlled conditions. A FT Applikon fermenter controller regulates these environmental conditions.

A Robbins device is used to study biofilm formation. The device provides quantifiable samples of biofilms growing on submerged surfaces in an aqueous environment which can be monitored over a time course. It consists of a hollow rectangular acrylic tube with twenty five evenly spaced sampling ports. Each port allows insertion of a sampling stud that contains a polyvinyl chloride (PVC) disk that lies flush to the upper surface of the lumen. The continuous culture is pumped through the Robbins device and biofilms are formed on the surface of PVC disks exposed to the culture. A series of Robbins devices may be run in each experiment. This allows the evaluation of different regimes to reduce biofilm development under identical controlled conditions.

1. Components of the Culture System

ACDP class III microbiological safety cabinet

Two litre glass chemostat vessel with a titanium top plate housed within the category III cabinet Stirrer housed within the class III microbiological safety cabinet Robbins Device (s) fastened to a Robbins device heater (Anglicon) housed within the class III microbiological safety cabinet 20 litre glass medium reservoir housed outside the class III microbiological safety cabinet 5 litre glass main effluent reservoir housed within the class III microbiological safety cabinet 1 litre glass effluent reservoirs connected to individual Robbins devices housed within the class III microbiological safety cabinet Glass alkaline reservoir housed outside the class III microbiological safety cabinet Applikon controller unit housed outside the class III microbiological safety cabinet (pH, temperature and Redox probes fitted within the chemostat)

Stand-alone personal computer housed outside the class III microbiological safety cabinet 2. Operation and Monitoring of the Chemostat i. A 10-ml aliquot of an 18 hour culture of *Pseudomonas aeruginosa*, at approximately 108 cfu per ml, was used to inoculate the sterile growth media within the chemostat. The inocula was introduced into the chemostat through the sample port in the top plate.

ii. Following inoculation, the chemostat was operated as a batch culture for 4 h to allow establishment of the culture.

iii. Medium addition (½ strength nutrient broth, Oxoid) was commenced at the desired flow rate (1 ml per min) and the effluent pump was activated. The flow rate of the effluent pump was the same as the inflow pump. The effluent tubing bypassed the Robbins devices leading straight to the main waste reservoir.

iv. The continuous chemostat was run for a predetermined time until a steady state was attained (96-hours). At this stage, the tubes leading to the Robbins devices were positioned onto the multi-head pump, thus instigating culture flow through the Robbins devices.

v. Planktonic culture samples (<5 ml) were removed from the chemostat daily for verification of pH and total viable counts, using a hand held vacuum pump connected to a sample port universal container.

vi. The area around the apparatus was checked twice daily (morning and afternoon) for spillage, and the vessel and tubing examined for leaks or splits.

vii. The medium, effluent and culture volumes were recorded on the run sheet and the flow rates calculated accordingly. The volume in the alkali reservoir was also recorded.

3. Robbins Device

Upstream of each Robbins device inlet tubes have a 'Y' junction. One line was designated as an inlet port (Port A) and is connected either to the chemostat or a sterile media reservoir. The other line was an inoculation port (Port B) that allowed the inoculation of the Robbins lumen with test agents.

Outlet tubes downstream of the Robbins device also have a 'Y' junction. One line was designated waste and led to a Robbins device waste reservoir (Port C). The other line led to a sterile universal container (UC) and was used to collect planktonic samples from the Robbins device lumen (Port D).

During initial biofilm development, the inoculation and planktonic sample ports were clamped (ports B and D) and the inlet line (A) was connected to the chemostat.

(i) Steady state culture was flowed through the Robbins device at 1 ml per min for a set time (24-hours) to allow the establishment of a biofilm on the PVC disks. At this time point, the multi-head pump was switched off, culture inlet tubing clamped and subsequently disconnected from the Robbins device at port A.

(ii) Tubing leading from the sterile growth media tubing was then connected to the Robbins device inlet port (A). The clamp on the media tubing was removed and the multi-head pump turned back on and allowed to run until the culture in the Robbins device lumen was replaced with ½ strength nutrient broth.

At this time point, studs (x3) were removed from the Robbins to enumerate biofilm density.

(iii) The multi-head pump was turned off and the inlet and outlet tubing clamped.

(iv) A stud was gently removed from Robbins device port and replaced with a sterile stud.

(v) The PVC coupon was carefully detached from the stud by unscrewing the retaining screw.

(vi) Holding the coupon with forceps, the under side of the coupon was rinsed in 1 ml sterile phosphate buffered saline (PBS) to remove loosely adhered cells.

(vii) The coupon was placed in 1 ml PBS contained in a eppendorf, sonicated for 3 min at 60 W, then vortex mixed for 2 min to disrupt the biofilm.

(viii) The coupon was aseptically removed to 5% sodium hypochlorite and the suspension serially diluted in sterile PBS up to 10-8.

(ix) The total viable count (cfu) of the biofilm population was determined using the method of Miles and Misra on tryptone soya agar (TSA).

The biofilm was then infected with bacteriophage/tobramycin or both simultaneously.

(x) With the media inlet port clamped (A), a 20 ml syringe containing 10 ml of bacteriophage at $10^9$ pfu per ml (or tobramycin) was aseptically connected to the inoculation port (B).

(xi) The clamp was removed from the inoculation port (B) and the planktonic sample outlet port (D), and the bacteriophage suspension/tobramycin solution injected into the Robbins device lumen.

(xii) Inoculation (B) and planktonic (D) ports were re-clamped and the device was left for 20 min to allow phage infection/tobramycin absorption of the biofilm.

(xiii) Following 20 min, the media inlet and waste reservoir clamps were released and the multi-head pump started to re-initiating flow of sterile media.

At predetermined time intervals (1 h, 2 h, 4 h, 6 h, 18 h, 12 h, 18 h, 24 h and 48 h) studs were removed from the Robbins device and replaced with sterile studs as stated in process iii-iv. Coupons were detached from the studs, sonicated and vortex mixed to remove biofilm as in process v-vii. Planktonic and biofilm associated bacteria and phage were then enumerated as stated below:

(xiv) The coupon was aseptically removed from the suspension to 5% sodium hypochlorite. An aliquot (250 µl) of the suspension was taken for centrifugation (13000 rpm for 5 min) and the supernatant, containing phage, serially diluted to $10^{-8}$. Phage titre was then determined using agar overlay plates with the corresponding host strain (section 4).

(xv) To the remaining suspension (750 µl), an adequate volume of ferrous ammonium sulphate (FAS) was introduced in order to achieve a 10 mM concentration and left for 10 min. This compound neutralises the free phage particles in the suspension, without effecting bacterial viability. The suspension was then serially diluted in sterile PBS up to $10^{-8}$.

(xvi) The total viable count (cfu) of the bacterial biofilm population was then determined using the method of Miles and Misra on tryptone soya agar.

4. Calculation of Bacteriophage Titre

Bacteriophage titre was calculated using an agar overlay infection with exponentially grown *Ps. aeruginosa*.

Preparation of Log Phase Culture (i) A test *Ps. aeruginosa* strain was streaked out onto a fresh TSA plate from a storage slope and incubated overnight (18 h) at 37° C.

(ii) Following incubation, the test *Ps. aeruginosa* strain (2-3 isolated colonies) was inoculated into 100 ml tryptone soya broth and incubated for 4 h at 37° C. with orbital aeration.

Agar Overlay Method (v) Soft agar, which had been prepared earlier, was re-melted and allowed to cool in a water bath set at 45° C.

(vi) Sterile tubes (12 mm diameter) were placed in a heating block set at 45° C. and left to acclimatise for 10 min.

(vii) Aliquots (2.5 ml) of soft agar were pipetted into each tube, followed by 500 µl of the 4 hour *Ps. aeruginosa* suspension and 100 µl of the serially diluted phage preparation. Controls were also prepared which contained soft agar only and soft agar and bacteria.

(viii) The suspensions were mixed then poured over pre-dried TSA plates. The plates were rocked gently to ensure a uniform layer of suspension, then left to dry on a level surface (20 mins). Once dried, the plates were incubated for 18 h at 37° C.

Following incubation, plates were then examined and the number of plaque forming units per ml recorded (pfu per ml).

5. Summary of Results

Biofilms of mucoid *Ps. aeruginosa* developed using a Robbins device were shown to be degraded by the administration of alg L carrying phage. FIGS. 1 and 2 show the effect of single (10-10 pfu per ml) and multiple doses (4×10-10 pfu per ml) of bacteriophage FGH4 on *Ps. aeruginosa* GH56 biofilms over a 24 hour period, which resulted in one and three Log reductions in biofilm populations respectively.

A series of multiple dose experiments were performed to compare the efficacy of biofilm removal with phage against tobramycin, a front line aminoglycoside antibiotic used to treat CF patients. Resultant data showed that four applications at the minimal inhibition concentration (MIC) over a 24 hour period had no significant effect on the *Ps. aeruginosa* sessile population (FIG. 3). This experiment was repeated with tobramycin at 10×MIC and again had no significant effect on biofilm viability.

A combined regime of phage φGH4 and tobramycin at the MIC level (FIG. 4) indicated a three-log reduction in biofilm cells, accompanied by a significant decrease in viability of released biofilm cells. Cells released through the action of phage disrupting the biofilm become susceptible to antibiotic activity.

Results

A) Isolation of Lytic Bacteriophage Against Clinical *Ps. aeruginosa* Strains:

Clinical samples were collected from Liverpool Medical School and screened against our 22 clinical *Ps. aeruginosa* strains and two control strains (NCTC 6750, ATCC 27853). A further 9 lytic bacteriophage were obtained from this study thus bringing the current phage collection to twenty. All isolated phage were enriched against their corresponding host and subsequently stored at 4° C. and −70° C.

B) Alginate Lysis:

At least three of the phage in the collection appeared to exhibit putative alginase activity. Using a turbidimetric procedure developed by Kitamikado et al. (1990) we have confirmed that these phage mediate the production of alginate lyase during the lytic cycle. The enzyme is present in phage induced cell lysates but is not found in uninfected cell lysates or in purified phage preparations.

C) In Vitro Biofilm Model:

Biofilms of mucoid *Ps. aeruginosa* developed using a Robbins device were shown to be degraded by the administration of phage. FIGS. 1 and 2 show the effect of single ($10^{10}$ pfu $ml^{-1}$) and multiple doses ($4 \times 10^{10}$ pfu $ml^{-1}$) of bacteriophage ΦGH4 on *Ps. aeruginosa* GH56 biofilms over a 48 hour period, which resulted in one and three log reductions in biofilm populations respectively.

A series of multiple dose experiments were performed to compare the efficacy of biofilm removal with phage against tobramycin, a front line aminoglycosidic antibiotic used to treat CF patients. Resultant data showed that four applications of minimal inhibition concentration (MIC) and 10×MIC Tobramycin over a 48 hour period had no significant effect on the *Ps. aeruginosa* sessile population.

When a dual infection regime of ΦGH4 and MIC tobramycin was tested a three-log reduction in biofilm cells was accompanied by a significant decrease in viability of released biofilm cells (i.e. *Ps. aeruginosa* cells released from the biofilm through the action of phage breaking open the biofilm).

D) Stability and Lytic Activity of Phage in Sputum:

To ensure effective treatment of cystic fibrosis pulmonary *Ps. aeruginosa* infections bacteriophage should exhibit lytic activity in the viscid sputum/mucin rich environment of the CF lung. In vitro phage infection assay performed with mucoid *Ps. aeruginosa* GH56 and phage ΦGH4 in sputum (free of indigenous *Ps. aeruginosa*) recovered from CF patients showed that the phage remains stable and retains greater than 90% lytic activity. Similar results were obtained with lytic infections performed in 5% mucin.

E) Stability and Lytic Activity of Phage Following Aerosolisation:

Delivery of phage to the CF lung preferably takes the form of a non-invasive inhalation system. Phage should therefore retain viability following aerosolisation. A Colison nebuliser coupled to a Henderson Apparatus was used to aerosolise a specific volume of a known titre of phage ΦGH4. This process generates aerosols in the region of 4 mm which are the optimum size for successful transportation to the alveoli at the base of the lungs. Resultant aerosols were collected, quantified and tested for lytic activity against *Ps. aeruginosa* GH56. Results showed that less than 5% of the phage were lost due to aerosolisation and that the phage retained >90% lytic activity against *P. aeruginosa* GH56 following passage through the Henderson Apparatus/Collison nebuliser.

Discussion

Twenty phage have been isolated from the environment and clinical specimens. The phage lyse clinical *Ps. aeruginosa* strains, which strains exhibit different host ranges.

Exopolysaccharide (EPS) normally protect bacterial biofilm cells against the majority of bacteriophage (Weiner et al., 1995). In the case of *Ps. aeruginosa* pulmonary infections, the bacterial biofilm is encapsulated within a thick alginate matrix. At least three of the phage we have isolated exhibit polysaccharide lyase (alginase) activity against a specific *Ps. aeruginosa* alginate. This is important in treating such infections, as the phage may illicit a two pronged attack on mucoid *Ps. aeruginosa* biofilms in degrading its way through the biofilm alginate thus gaining access to the underlying susceptible bacteria. The turbidimetric alginase assay confirms that the enzyme is only present during the lytic cycle of phage infection, and we have confirmed that the alginase activity is phage encoded.

FIG. 1 shows the effect of one dose of bacteriophage φGH4 on an established 24 hour *Ps. aeruginosa* GH 56 biofilm in the in vitro biofilm model. The results indicate that a single dose of phage caused a 1 log reduction in biofilm associated *Ps. aeruginosa*. The numbers of biofilm associated *Ps. aerugi-* nosa however began to rise following 6 hours infection with phage. The rate of growth of biofilm *Ps. aeruginosa* at this time was similar to the control model. We hypothesised that this phenomenon could possibly be caused by washout of the phage from the biofilm (i.e. biofilm rupture resulting in the release of phage into the planktonic phase). To reduce the likelihood of phage washout, it was decided to investigate the effect of multiple doses of phage (4 doses at six hour intervals for the first 18 hours of the experiment) on the *Ps. aeruginosa* biofilm (FIG. 2). Initial phage infection reduced the biofilm community by 1 log. A further 1.75 log reduction was achieved when the second dose of phage was administered.

Of great interest are the results obtained with dual therapy of bacteriophage and tobramycin. We hypothesised that removal of *Ps. aeruginosa* cells from the alginate rich biofilm environment renders the previously resistant cells sensitive to tobramycin. This infection regime therefore generates a synergistic effect on *Ps. aeruginosa* both within the biofilm and bacilli released from the biofilm through the action of alginate lyase phage.

The observation that phage infection and cell lysis was not inhibited in the presence of sputum or by the process of aerosolisation demonstrates that the inhalation conveyance system of phage aerosols would ensure delivery of viable lytic phage into the sputum rich lung alveoli of CF patients.

EXAMPLE 2

Preparation of a Bacteriophage Containing a Heterologous Polysaccharide Lyase

Method for the insertion of a heterologous alginase gene into a bacteriophage.
(i) Determine the DNA sequence of the bacteriophage genome. This is achieved by partial digestion of the bacteriophage DNA with a restriction enzyme that cuts frequently. Frequent cutters are usually those that recognise tetrameric restriction sites. The partially digested DNA is size fractionated on an agarose gel and fragments of 500 to 2000 bp then cloned into a suitable plasmid vector such as pUC18, transformed into an *E. coli* host and grown on selective media. Individual colonies are isolated and the plasmid DNA recovered for DNA sequencing of the bacteriophage DNA fragment carried. Sequencing of clones is continued until a continuous DNA sequence map has been compiled. Any sequence gaps that persist can be closed by chromosome walking ie using primers designed to bacteriophage DNA sequence close to the gaps, identifying clones that contain that sequence by probing and then using that primer in the DNA sequencing reaction.

(ii) Annotate the genome sequence to identify open reading frames (orfs) and associated promoters/termination sites. Programmes are publically available either on the internet eg ORF finder or in the DNAstar suite of programmes which identify open reading frames and enable putative identification of function by comparison with DNA sequence databases.

(iii) Create a physical map to identify restriction sites suitable for cloning in the alginase gene. DNA sequence data enables the identification of every known restriction site for which there is a restriction enzyme available within the DNA sequence. Physical maps illustrating the position of every restriction site can be created in programmes such as MapDraw from the DNAstar suite of programmes. Taken together with the annotation of the DNA sequence, regions can be identified which contain useful restriction sites but do not contain ORFs and are therefore less likely to interfere with bacteriophage propagation.

(iv) Identify heterologous alginase gene from selected bacteria or bacteriophage for cloning into therapeutic bacteriophage. A suitable heterologous gene is provided by the bacterium *Azotobacter chroococcum*, which may be readily cloned using one of two methods.

Where the DNA sequence of the lyase (eg. alginase) gene has been determined, direct cloning may be employed by PCR using a primer designed upstream of the sequence and a complementary reverse primer downstream. For the *A. chroococcum* algL gene, the DNA sequence is publically available on Genbank under Accession No. AJ223605, and a pair of suitable primers includes GGACTGAACTTCTTCGCC (SEQ ID NO: 1) (forward primer) and GCTGCTGCTGGATCGGC (SEQ ID NO: 2) (reverse primer). The primers may further comprise restriction sites at their 5' ends to facilitate cloning. These primers are suitable for PCR amplification of the complete lyase (eg. algL gene from *A. chroococcum*) using a proof-reading DNA polymerase to ensure the cloning of a active gene product. A conventional alginase assay is then employed to confirm the presence of alginase activity.

The second method is employed where the relevant DNA data are not available, and involves the preparation of a gene library of the selected bacteria or bacteriophage containing the alginase in a plasmid such as pUC19 in *E. coli*. The gene library is then screened for alginase activity by a conventional alginase assay, and the clone carrying the alginase gene identified.

(v) Clone the alginase gene in to each useful site in the bacteriophage DNA in vitro and transform in to the host using a suitable procedure which may be transformation, conjugation or electroporation. Useful sites do not necessarily have to be unique as it is possible to partially digest with a restriction enzyme such that not all the restriction sites are cut.

(vi) Confirm bacteriophage retain viability as evidenced by the ability to form plaques.

(vii) Screen phage induced cell lysates for evidence of expression of recombinant alginase activity.

(viii) Alternatively a marker can be used (lac or GFP for example) if checking for the additional alginase activity is not straight forward.

(ix) If no suitable unique site is found an appropriate site may be created using site directed mutagenesis based on a PCR approach.

EXAMPLE 3

To Confirm that a Given Bacteriophage is Capable of Infecting a Bacterium Identified within a Biofilm Isolation of *Pseudomonas aeruginosa* and *Burkholderia cepacia* from Clinical Samples (i) Aliquots (100 μl) of the clinical sample (e.g. sputum, pulmonary lavage) are spread onto tryptone soya agar (TSA, Oxoid), *Pseudomonas* CN agar (Oxoid, selective for *P. aeruginosa*), *Pseudomonas* CFC (Oxoid, selective for *Pseudomonas* species) and *Pseudomonas cepacia* agar (Oxoid, selective for *Burkholderia cepacia*), and allowed to dry for 10 min.

(ii) TSA and *Pseudomonas* CN agar plates are incubated at 37° C. for 24 h. If no growth is recorded, plates are incubated for a further 24 h (48 h total incubation).

(iii) *Pseudomonas* CFC plates and *P. cepacia* plates are incubated at 30° C. and examined after 24 h, 48 h and if necessary 72 h incubation.

Any growth on *Pseudomonas* CFC medium indicates the presence of *Pseudomonas* spp. The presence of blue/green or brown pigmentation may be taken as presumptive evidence of *P. aeruginosa*.

Growth on *Pseudomonas* CN medium indicates presence of *P. aeruginosa*.

B. *cepacia* typically grows as smooth, glistening red/purple colonies of approximately 2 mm diameter on *P. cepacia* media. Specific strains may grow as atypical forms including lipolysaccharide deficient strains with dwarf, rough colonial appearance and a diffusible brown melanin-like pigmentation.

(iv) Isolated colonies are plated onto TSA and the original selective media, then incubated at 37° C. (or 30° C. depending on the isolation media) for conformation of purity. Once purity is confirmed, the test isolate is inoculated onto a TSA slope and stored at 4° C.

Our collection of bacteriophage can now be examined for lytic activity against the test isolate using the agar overlay method.

Preparation of Log Phase Culture (v) The test isolate is streaked out onto a fresh TSA plate from a storage slope and incubated overnight (18 h) at 37° C.

(vi) Following incubation, the test strain (2-3 isolated colonies) is inoculated into 100 ml tryptone soya broth and incubated for 4 h at 37° C. with orbital aeration.

Agar Overlay Method (vii) Soft agar, which has been prepared earlier, is re-melted and allowed to cool in a water bath set at 45° C.

(viii) Sterile tubes are placed in a heating block set at 45° C., and left to acclimatise for 10 min.

(ix) Aliquots (2.5 ml) of soft agar are pipetted into each tube, followed by 500 µl of the 4 h test suspension and 100 µl of our serially diluted phage preparation. Controls are also prepared which contain soft agar only and soft agar and bacteria.

(x) The suspensions are gently vortex mixed, then poured over pre-dried TSA plates. The plates are rocked gently to ensure a uniform layer of suspension, then left to dry on a level surface (20 mins). Once dried, the plates are incubated for 18 h at 37° C.

Following incubation, plates are then examined for lysis, and the number of plaque forming units per ml recorded (pfu $ml^{-1}$).

EXAMPLE 4

To Confirm that a Given Polysaccharide Lyase is Capable of Degrading a Biofilm Component Isolation of Biofilm Alginate Bacterial constituents of the biofilm must firstly be isolated as a pure culture (see Example 3; Isolation of *Pseudomonas aeruginosa* and *Burkholderia cepacia* from clinical samples).

(i) The test isolate is streaked out onto a fresh tryptone soya agar (TSA) plate from a storage slope and sealed. The plate is then incubated for 48 h at 37° C.

(ii) Following incubation, the resulting mucoid growth is removed from the surface using a sterile glass spreader, and suspended in sterile distilled water.

(iii) The suspension is vortex mixed, then centrifuged (13000 rpm) for 1 h at 4° C.

(iv) The alginate containing supernatant is then decanted into a sterile tube, Three volumes of absolute alcohol (v/v) are added to the supernatant and left to stand at 4° C. for 45 min, thus allowing the alcohol to precipitate the exopolysaccharide.

(v) The suspension is then centrifuged 5000 rpm for 10 min, and the precipitated exopolysaccharide re-suspended in sterile distilled water producing a viscous solution.

Our test alginate lyase preparation/bacteriophage carrying alginate lyase is then examined for its ability to lyse clinically isolated alginate using the turbidimetric procedure developed by Kitamikado et al. (1990).

EXAMPLE 5

In Vivo Therapy

Mice were infected with *Ps. aeruginosa* at day zero, and the infection allowed to establish. The average recovery of *Ps. aeruginosa* from infected mice (n=6) was 4.28±0.59 Log $CFU.ml^{-1}$.

At day 10 mice were exposed to aerosolised bacteriophage. Phage and bacteria were then recovered from the mice at 6 and 24 hours post-aerosol challenge (see FIG. 5).

Phage Counts

Recovery of phage at 6 h=5.97±0.34 Log $CPU.ml^{-1}$.
Recovery of phage at 24 h=5.05±1.91 Log $PFU.ml^{-1}$.

*Pseudomonas* Counts

*Pseudomonas* recovered after 6 h=0.53±0.83 Log $CFU.ml^{-1}$.

*Pseudomonas* recovered after 24 h=0.0.57±1.04 Log $CFU.ml^{-1}$.

Results

Results demonstrate a decrease of 3.75 Log $CFU.ml^{-1}$ in the number of *Ps. aeruginosa* after challenge with bacteriophage. These results are significantly different (P<0.05).

REFERENCES

Barrow, P., Lovell, M. & Berchieri, A., Jr. (1998). Use of lytic bacteriophage for control of experimental *Escherichia coli* septicemia and meningitis in chickens and calves. *Clin Diagn Lab Immunol* 5, 294-8.

Biswas, B., Adhya, A., Washart, P., Paul, B., Trostel, A., Powell, B., Carlton, R., Merril, C. (2002). Bacteriophage Therapy rescues mice bacteremic from a clinical isolate of vancomycin-resistant *Enterococcus faecium*, *Infect. Imm.* 70, 204-210, Doolittle, M. M., Cooney, J. J. & Caldwell, D. E. (1996). Tracing the interaction of bacteriophage with bacterial biofilms using fluorescent and chromogenic probes. *J Industrial Microbiol* 16, 331-41

Doolittle, M. M., Cooney, J. J., & Cadwell D. E., (1995). Lytic infection of *Escherichia coli* biofilms by bacteriophage T4. *J Microbiology* 41, 2-18.

Hancock, R. E. and Chapple, D. S. (1999). *Antimicrobial Agents and Chemotherapy* 43 (6), 1317-1323.

Hanlon, G. W., Denyer, S. P., Olliff, C. J., and Ibrahim L. J., (2001). Reduction in exopolysaccharide viscosity as an aid to bacteriophage penetration through *Pseudomonas aeruginosa* biofilms. *App. Env. Micro.* 67, 2746-2753.

Hughes, K. A., Sutherland, I. W. and Jones, M. V. (1998). Biofilm susceptibility to bacteriophage attack: the role of phage-borne polysaccharide polymerase. *Microbiol.* 144, 3039-3047.

Kitamikado, M., Yamaguchi, K., Tseng, C. H. & Okabe, B. (1990). Method designed to detect alginate-degrading bacteria. *Appl. Environ. Microbiol.* 56, 2939-2940.

Roy, B., Ackermann, H. W., Pandian, S., Picard, G. & Goulet, J. (1993). Biological inactivation of adhering *Listeria monocytogenes* by listeriaphages and a quaternary ammonium compound. *Appl Environ Microbiol* 59, 2914-7.

Smith, H. W. & Huggins, M. B. (1983). Effectiveness of phages in treating experimental *Escherichia colidiarrhoea* in calves, piglets and lambs. *J Gen Microbiol* 129, 2659-75.

Smith, H. W., Huggins, M. B. & Shaw, K. M. (1987). The control of experimental *Escherichia coli* diarrhoea in calves by means of bacteriophages. *J Gen Microbiol* 133, 1111-26.

Soothill, J. S. (1992). Treatment of experimental infections of mice with bacteriophages. *J Med Microbiol* 37, 258-61.

Soothill, J. S. (1994). Bacteriophage prevents destruction of skin grafts by *Pseudomonas aeruginosa*. *Burns* 20, 209-11.

Sutherland, I. W., Skillman, L. C. and Hughes, K. A. (1999). Polysaccharides in biofilms and their interactions with phage and antimicrobials, In *Biofilms* pp. 179-187, Edited by J. Wimpenny, P. Gilbert, J. Walker, M. Brading and R. Bayston, Cardiff:Bioline.

Tait, K., Skillman, L. C., and Sutherland, I. W. (2002). The efficacy of bacteriophage as a method of biofilm eradication. *Biofouling* 18(4), 305-311.

Weiner, R., Langille, S. and Quintero, E (1995). Structure, function and immunochemistry of bacterial exopolysaccharides. *J Ind Microbiol* 15, 339-346.

enzyme that is capable of degrading a polysaccharide within said biofilm, and a pharmaceutically-acceptable antimicrobial agent, wherein the biofilm includes a *Pseudomonas* sp., the first bacteriophage is capable of infecting said *Pseudomonas* sp., and the first bacteriophage is selected from the group consisting of GH4 (ECACC Accession No. 02121203), GH6 (ECACC Accession No. 02121202), GH13 (ECACC Accession No. 02121201), GH14 (ECACC Accession No. 02121204); and a bacteriophage having accession No. ATCC 12055-B1, ATCC 12055-B2, ATCC 12055-B3, ATCC 14205-B1, ATCC 14206-B1, ATCC 14207-B1, ATCC 14209-B1, ATCC 14210-B1, ATCC 14211-B1, ATCC 14212-B1, ATCC 14213-B1, ATCC 14214-81, ATCC 15692-B2, ATCC 15692-B3, ATCC 25102-B1, ATCC BAA-26-B1, ATCC BAA-27-B1, ATCC BAA-28-B1, ATCC BAA-28-B2, ATCC BAA-29-B1, ATCC BAA-30-B1, ATCC BAA-31-B1, ATCC BAA-47-B1, ATCC BAA-79-B1, ATCC BAA-81-B1, and ATCC BAA-81-B2.

2. A composition according to claim 1, wherein the pharmaceutically acceptable antimicrobial agent is an antibiotic.

3. A composition according to claim 1, further comprising a DNase.

4. A composition according to claim 1, further comprising a second polysaccharide lyase, wherein the first and second polysaccharide lyase are different.

5. A composition according to claim 1, wherein the first polysaccharide lyase is encoded by the bacteriophage.

6. A composition according to claim 1, wherein the bacteriophage encodes one or more of a pharmaceutically-accept-

The invention claimed is:

1. A composition for treating a bacterial biofilm wherein the biofilm is a biofilm of a patient, said composition comprising a first bacteriophage that is capable of infecting a bacterium within said biofilm, a first polysaccharide lyase able antimicrobial agent, a DNase, or a second polysaccharide lyase that is different from the first polysaccharide lyase.

7. A composition according to claim 1, comprising a second bacteriophage, which is different from the first bacteriophage, and wherein the second bacteriophage optionally encodes a second polysaccharide lyase.

8. A composition according to claim 1, comprising a second pharmaceutically-acceptable antimicrobial agent.

9. A composition according to claim 1, wherein the first bacteriophage encodes said first polysaccharide lyase.

10. A composition according to claim 1, further comprising a second bacteriophage selected from the group consisting of GH4 (ECACC Accession No. 02121203), GH6 (ECACC Accession No. 02121202), GH13 (ECACC Accession No. 02121201), and GH14 (ECACC Accession No. 02121204), wherein the first bacteriophage and second bacteriophage are different.

11. A composition according to claim 1, wherein the first bacteriophage comprises a heterologous gene encoding a first polysaccharide lyase enzyme.

12. A composition according to claim 4, wherein the first and/or second polysaccharide lyase is an alginate lyase.

13. A composition according to claim 1 in the form of an aerosol formulation, comprising one or more of an excipient, surfactant, and/or propellant.

14. A method of treating a biofilm infection, wherein the biofilm is a biofilm of a patient, comprising administering to a patient:
   a first bacteriophage capable of infecting a bacterium within said biofilm;
   a first polysaccharide lyase enzyme capable of degrading a polysaccharide within said biofilm; and
   a pharmaceutically-acceptable antimicrobial agent,
   wherein the biofilm includes a *Pseudomonas* sp.,
   the first bacteriophage is capable of infecting said *Pseudomonas* sp., and the first bacteriophage is selected from the group consisting of GH4 (ECACC Accession No. 02121203). GH6 (ECACC Accession No. 02121202), GH13 (ECACC Accession No. 02121201), GH14 (ECACC Accession No. 02121204); and a bacteriophage having accession No. ATCC 12055-B1, ATCC 12055-B2, ATCC 12055-B3, ATCC 14205-B1, ATCC 14206-B1, ATCC 14207-B1, ATCC 14209-B1, ATCC 14210-B1, ATCC 14211-B1, ATCC 14212-B1, ATCC 14213-B1, ATCC 14214-81, ATCC 15692-B2, ATCC 15692-B3, ATCC 25102-B1, ATCC BAA-26-B1, ATCC BAA-27-B1, ATCC BAA-28-B1, ATCC BAA-28-B2, ATCC BAA-29-B1, ATCC BAA-30-B1, ATCC BAA-31-B1, ATCC BAA-47-B1, ATCC BAA-79-B1, ATCC BAA-81-B1, and ATCC BAA-81-B2.

15. A method according to claim 14, wherein the pharmaceutically-acceptable antimicrobial agent is an antibiotic.

16. A method according to claim 14, further comprising administering DNase.

17. A method according to claim 14, further comprising administering a second polysaccharide lyase, wherein the first and second polysaccharide lyase are different.

18. A method according to claim 14, wherein the bacteriophage encodes one or more of a pharmaceutically-acceptable antimicrobial agent, a DNase, or a second polysaccharide lyase that is different from the first polysaccharide lyase.

19. A method according to claim 14, comprising administering a second bacteriophage, which is different from the first bacteriophage, and wherein the second bacteriophage optionally encodes a second polysaccharide lyase.

20. A method according to claim 14, comprising administering a second pharmaceutically-acceptable antimicrobial agent.

21. A method according to claim 14, wherein the first bacteriophage is a GH bacteriophage and encodes said first polysaccharide lyase.

22. A method according to claim 14, further comprising administering a second bacteriophage selected from the group of GH4 (ECACC Accession No. 02121203), GH6 (ECACC Accession No. 02121202), GH13 (ECACC Accession No. 02121201), and GH14 (ECACC Accession No. 02121204), wherein the first bacteriophage and second bacteriophage are different.

23. A method according to claim 14, wherein the first bacteriophage comprises a heterologous gene encoding a first polysaccharide lyase enzyme.

24. A method according to claim 17, wherein the first and/or second polysaccharide lyase is an alginate lyase.

25. A method according to claim 14 comprising administering said first bacteriophage, said first polysaccharide lyase and said pharmaceutically-acceptable antimicrobial agent in the form of an aerosol formulation, comprising one or more of an excipient, surfactant, and/or propellant.

26. A method according to claim 14, wherein following administration the bacterial cell count of the biofilm is reduced by at least one log.

27. A method according to claim 14, wherein the composition or first bacteriophage is administered in more than one separate dose.

28. A method according to claim 14, wherein the composition or first bacteriophage is administered in at least three separate doses.

29. A method according to claim 14, wherein the first bacteriophage is administered prior to or subsequent to the first polysaccharide lyase.

30. A method according to claim 14, wherein the first bacteriophage is administered prior to, or subsequent to said pharmaceutically-acceptable antimicrobial agent.

31. A method according to claim 14, wherein the first bacteriophage is administered prior to or subsequent to a second polysaccharide lyase that is different from the first polysaccharide lyase.

32. A method according to claim 14, wherein the first bacteriophage is administered prior to or subsequent to a second bacteriophage that is capable of infecting a bacterium within the biofilm, wherein said second bacteriophage is different from the first bacteriophage.

33. A composition according to claim 1, wherein the biofilm is a lung biofilm of a cystic fibrosis patient.

34. A method according to claim 14, wherein the biofilm is a lung biofilm of a cystic fibrosis patient.

35. A composition according to claim 1, wherein the patient is an animal.

36. A composition according to claim 1, wherein the patient is a human.

37. A method according to claim 14, wherein the patient is an animal.

38. A method according to claim 14, wherein the patient is a human.

39. A method according to claim 14, wherein following administration the bacterial cell count of the biofilm is reduced by at least three logs.

40. A composition according to claim 1, wherein
   the pharmaceutically-acceptable antimicrobial agent is active against said *Pseudomonas* sp.

* * * * *

UNITED STATES PATENT AND TRADEMARK OFFICE
CERTIFICATE OF CORRECTION

| | | |
|---|---|---|
| PATENT NO. | : 7,758,856 B2 | Page 1 of 1 |
| APPLICATION NO. | : 10/541716 | |
| DATED | : July 20, 2010 | |
| INVENTOR(S) | : Gavin Hughes et al. | |

It is certified that error appears in the above-identified patent and that said Letters Patent is hereby corrected as shown below:

In the claims:

Col. 22, line 4, please delete "sp" and insert --*sp*--.
Col. 22, line 6, please delete "sp" and insert --*sp*--.
Col. 23, line 28, please delete "sp" and insert --*sp*--.
Col. 23, line 30, please delete "sp" and insert --*sp*--.
Col. 24, line 62, please delete "sp" and insert --*sp*--.

Signed and Sealed this
Twenty-sixth Day of April, 2011

David J. Kappos
*Director of the United States Patent and Trademark Office*

UNITED STATES PATENT AND TRADEMARK OFFICE
CERTIFICATE OF CORRECTION

Page 1 of 1

PATENT NO. : 7,758,856 B2
APPLICATION NO. : 10/541716
DATED : July 20, 2010
INVENTOR(S) : Gavin Hughes et al.

It is certified that error appears in the above-identified patent and that said Letters Patent is hereby corrected as shown below:

Front Page:

Please delete after Assignee: "Biocontrol Limited, Southampton (GB)" and insert --Health Protection Agency, Salisbury (GB)--.

Signed and Sealed this
Twenty-third Day of October, 2012

David J. Kappos
*Director of the United States Patent and Trademark Office*